(12) United States Patent
Parker et al.

(10) Patent No.: US 7,004,946 B2
(45) Date of Patent: *Feb. 28, 2006

(54) ACETABULAR CUP IMPACTOR

(75) Inventors: Brad A. Parker, Warsaw, IN (US);
Reese K. Myers, Warsaw, IN (US)

(73) Assignee: Symmetry Medical, Inc., Warsaw, IN (US)

( * ) Notice: Subject to any disclaimer, the term of this patent is extended or adjusted under 35 U.S.C. 154(b) by 87 days.

This patent is subject to a terminal disclaimer.

(21) Appl. No.: 10/283,993

(22) Filed: Oct. 30, 2002

(65) Prior Publication Data

US 2003/0050645 A1    Mar. 13, 2003

(51) Int. Cl.
A61B 17/58 (2006.01)
A61F 2/00 (2006.01)
A61F 2/34 (2006.01)

(52) U.S. Cl. ...................................................... 606/99
(58) Field of Classification Search ................. 606/53, 606/86, 91, 99, 100, 79, 80, 81; 623/22.23
See application file for complete search history.

(56) References Cited

U.S. PATENT DOCUMENTS

| | | | | |
|---|---|---|---|---|
| 3,961,620 A | * | 6/1976 | Schack et al. | 600/570 |
| 4,293,962 A | * | 10/1981 | Fuson | 606/95 |
| 4,362,520 A | | 12/1982 | Perry | 464/149 |
| 4,706,659 A | * | 11/1987 | Matthews et al. | 606/80 |
| 5,116,339 A | * | 5/1992 | Glock | 606/91 |
| 5,169,399 A | | 12/1992 | Ryland et al. | 606/91 |
| 5,322,505 A | * | 6/1994 | Krause et al. | 604/24 |
| 5,395,188 A | * | 3/1995 | Bailey et al. | 408/127 |
| 5,431,657 A | | 7/1995 | Rohr | 606/91 |
| 5,540,697 A | | 7/1996 | Rehmann et al. | 606/91 |
| 5,571,200 A | | 11/1996 | Cohen et al. | 623/22 |
| 5,584,837 A | | 12/1996 | Petersen | 606/91 |
| 5,630,819 A | | 5/1997 | Ashby et al. | 606/81 |
| 5,683,399 A | * | 11/1997 | Jones | 606/91 |
| 5,830,215 A | * | 11/1998 | Incavo et al. | 606/79 |
| 5,902,107 A | * | 5/1999 | Lowell | 433/130 |
| 5,908,423 A | * | 6/1999 | Kashuba et al. | 606/80 |
| 6,010,508 A | | 1/2000 | Bradley | 606/86 |
| 6,053,922 A | | 4/2000 | Krause et al. | 606/80 |
| 6,063,124 A | * | 5/2000 | Amstutz | 623/22.21 |
| 6,093,184 A | * | 7/2000 | Campbell et al. | 606/1 |
| 6,174,313 B1 | * | 1/2001 | Bonutti | 606/80 |
| 6,178,354 B1 | * | 1/2001 | Gibson | 607/116 |
| 6,200,306 B1 | * | 3/2001 | Klostermeyer et al. | 606/1 |
| 6,312,438 B1 | * | 11/2001 | Adams | 606/159 |
| 6,447,518 B1 | * | 9/2002 | Krause et al. | 606/80 |
| 6,613,085 B1 | * | 9/2003 | Anderson et al. | 623/2.11 |
| 6,743,237 B1 | * | 6/2004 | Dhindsa | 606/127 |
| 2003/0229356 A1 | * | 12/2003 | Dye | 606/99 |

* cited by examiner

Primary Examiner—Eduardo C. Robert
Assistant Examiner—Anu Ramana
(74) Attorney, Agent, or Firm—Taylor & Aust, P.C.

(57) ABSTRACT

An acetabular cup impactor particularly suited for minimally invasive surgical procedures includes a handle, a shaft assembly and a coupler connectable to an acetabular cup. The shaft assembly includes a hollow outer shaft and a flexible drive shaft disposed in the outer shaft. The flexible drive shaft is connected at one end to the coupler, and at an opposite end to a thumb wheel, such that rotation of the thumb wheel rotates the drive shaft and operates the coupler. The shaft assembly is curved to bypass anatomical structures intervening between a surgical incision and the acetabulum of a patient.

20 Claims, 2 Drawing Sheets

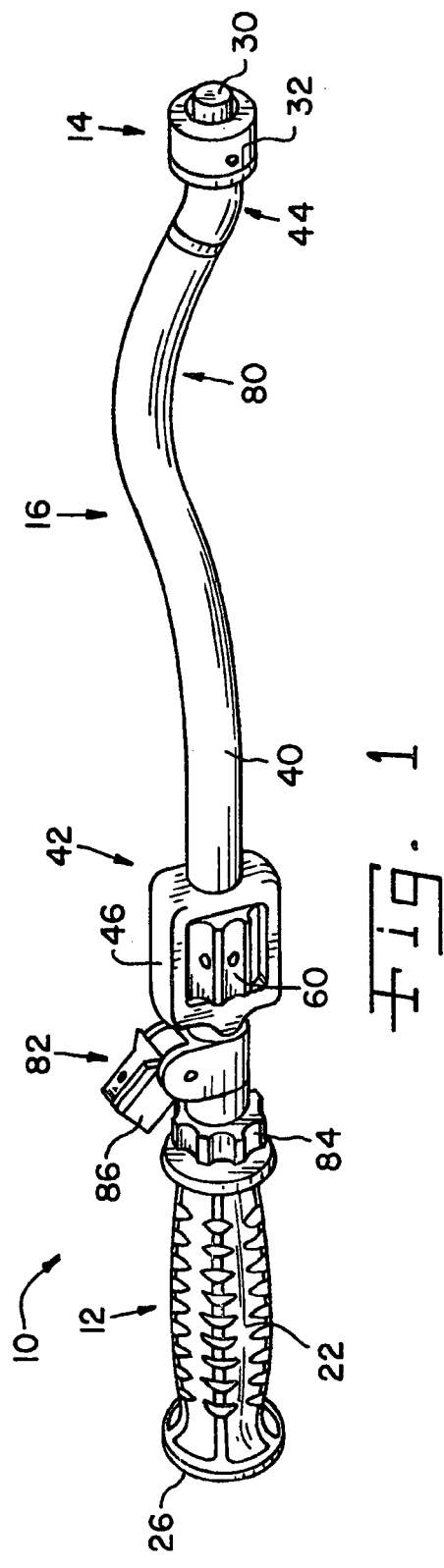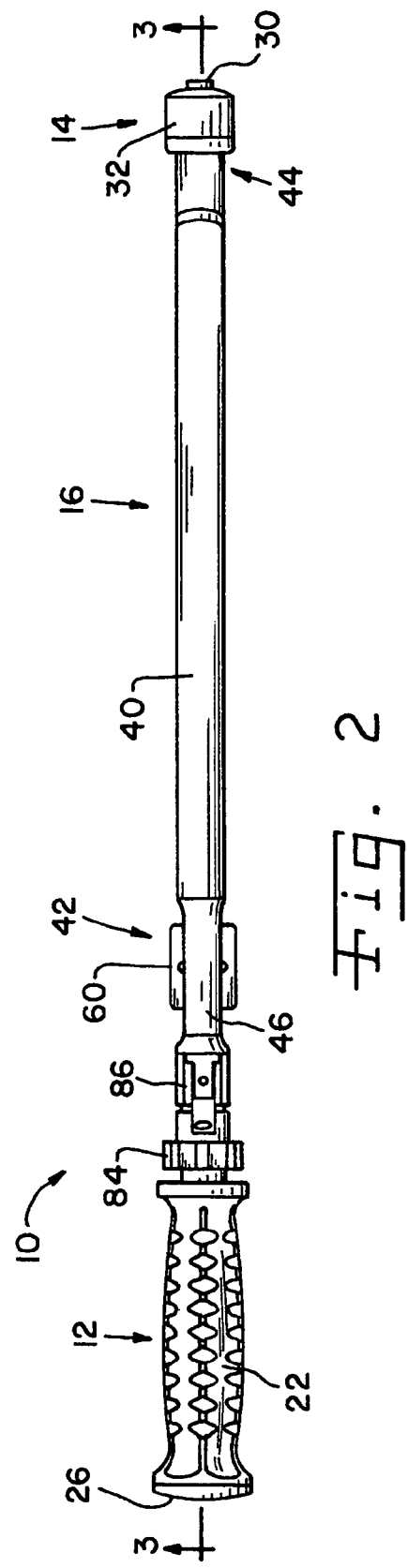

ACETABULAR CUP IMPACTOR

BACKGROUND OF THE INVENTION

1. Field of the Invention

The present invention pertains generally to surgical instruments and, more particularly, to surgical instruments such as an acetabular cup impactor particularly suited for use in minimal invasive surgical procedures.

2. Description of the Related Art

Early techniques for performing major orthopedic surgical procedures, such as joint replacements or reconstructions, included making large incisions and exposing the entire joint. Even with a successful surgery, the trauma to the patient is significant from open surgical procedures. As a result, rehabilitation periods are long and require dedication from the patient over an extended difficult time period to ensure the best possible result. Even with a skilled surgeon and a patient committed to a rehabilitation program, it is not always possible to achieve the desired results due in part to the surgical damage to areas surrounding the joint and the extensive scaring that can result.

In an effort to reduce trauma caused by open surgical procedures, it is desirable to reduce the size of incisions. Some procedures, such as many procedures performed on knees, now are routinely performed arthroscopically. Small incisions are made at discrete locations around the knee, and surgical tools are inserted through the incisions for performing the required procedures. Inspection of the joint, and observation of the procedure are achieved remotely, using fiber optics inserted through one of the incisions to illuminate the site and display a picture thereof on a view screen.

Procedures for knees and some other joints are readily adaptable to arthroscopic performance, using essentially straight, inline surgical tools. However, procedures for some other joints, such as hips, are not as easily adapted to minimally invasive surgical procedures. Because of surrounding hard and soft tissue structures, it is difficult to position properly inline surgical tools through incisions spaced about the joint. For example, to set an acetabular cup in a properly prepared acetabulum, an acetabular cup impactor is used. An surgical implement coupler of the impactor is secured to the acetabular cup. An elongated shaft is joined to the surgical implement coupler at one end, and includes a striker cap at the opposite end of the shaft. The cup is seated in the prepared acetabulum by positioning the cup in the prepared depression, and imparting a series of blows from a mallet against the striker cap. The force of the blows is transmitted through the shaft of the impactor, to seat the cup in the prepared opening in the acetabulum. After the cup is properly seated, the surgical implement coupler of the impactor is detached from the cup.

Two problems occur in seating an acetabular cup in this manner during a minimally invasive procedure. It is difficult to properly align the impactor because of anatomical features that are in the way, and disconnecting the head from the cup is more difficult with limited access to the end of the tool.

As a consequence, many common hip procedures, such as total hip replacements, are routinely performed through large incisions, in open procedures, exposing the entire joint, with the increased trauma caused thereby perceived as a necessary disadvantage.

What is needed in the art is an acetabular cup impactor that is more easily used during minimally invasive procedures.

SUMMARY OF THE INVENTION

The present invention provides an acetabular cup impactor with a curved shaft that makes proper alignment of the tool more easily accomplished during a minimally invasive surgical procedure, and a remotely activated surgical implement coupler for disengaging the head from an acetabular cup.

The invention comprises, in one form thereof, a surgical tool for connecting to a surgical implement. The surgical tool is provided with a hollow elongated outer shaft having a first end and a second end, and a curved portion between the first and second ends. A handle is provided at one the end of the outer shaft, and an implement coupler is provided at the other the end of the outer shaft. The coupler is adapted for selectively engaging and disengaging a surgical implement. A flexible drive shaft is disposed in the outer shaft, with one end of the drive shaft connected to the coupler for operating the coupler by rotation of the drive shaft. A manual activation device is provided for rotating the drive shaft to selectively operate the coupler. The manual activation device is disposed near the handle.

The invention comprises, in another form thereof, an orthopedic impactor provided with an elongated hollow outer shaft, a coupler at one end of the outer shaft adapted for engaging an orthopedic implant; and a handle disposed at an end of the hollow outer shaft opposite from the coupler. A striker plate is disposed on the handle, and is adapted for receiving blows from a mallet. A flexible drive shaft is disposed in the outer shaft and connected to the coupler. A rotary input device is provided for rotating the drive shaft to operate the coupler.

In still another form thereof, the invention comprises an acetabular cup impactor, provided with a hollow rigid outer shaft having at least a portion defining a curved shape; a coupler at one end of the shaft adapted for rotation to be engaged to and disengaged from an acetabular cup; a handle at an opposite end of the shaft from the coupler. The handle has an exposed end and a striker plate on the exposed end. A flexible drive shaft in the outer shaft is connected to the coupler for rotating the coupler. A drive means near the handle is provided for rotating the drive shaft to operate the coupler.

An advantage of the present invention is providing an acetabular cup impactor that facilitates seating an acetabular cup during a minimally invasive surgical procedure.

Another advantage is providing an acetabular cup impactor that circumvents intervening anatomical structures to properly position an acetabular cup, and that imparts seating force to the cup in a properly aligned direction.

Yet another advantage is providing an acetabular cup impactor that is easy to use, and that can be disengaged from an acetabular cup even without having the end of the impactor directly accessible.

BRIEF DESCRIPTION OF THE DRAWINGS

The above-mentioned and other features and advantages of this invention, and the manner of attaining them, will become more apparent and the invention will be better understood by reference to the following description of an embodiment of the invention, taken in conjunction with the accompanying drawings, wherein:

FIG. 1 is a perspective view of the acetabular cup impactor of the present invention;

FIG. 2 is a top plan view of the acetabular cup impactor shown in FIG. 1; and

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 3:
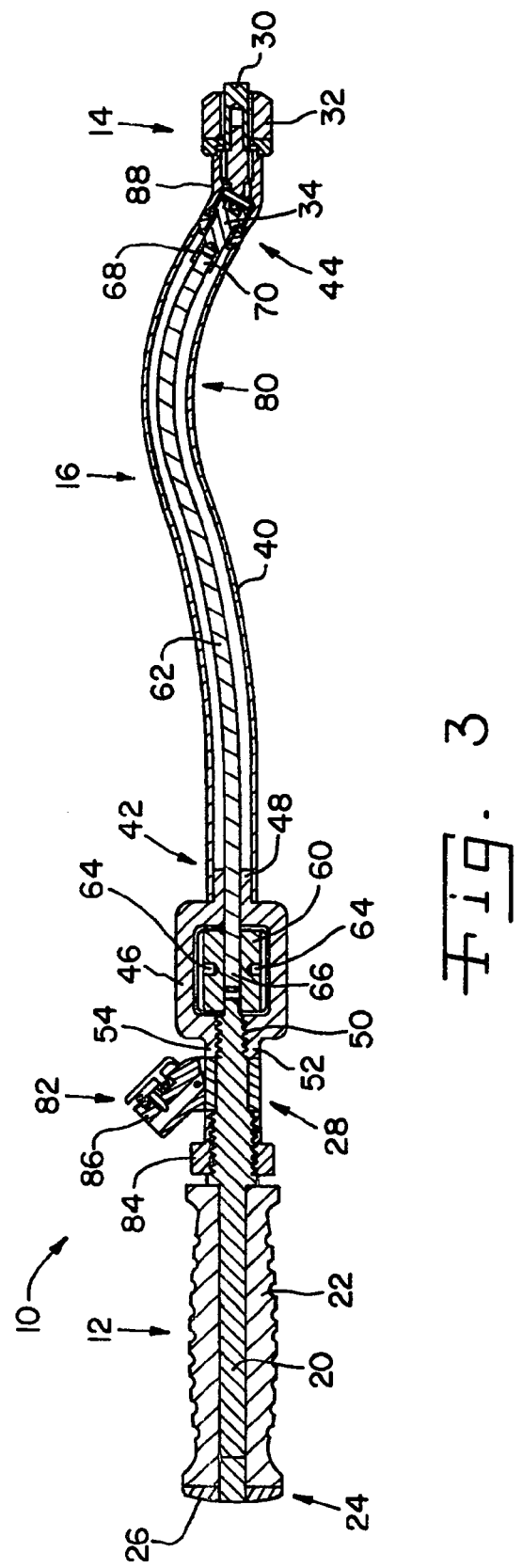
FIG. 3 is a cross-sectional view of the acetabular cup impactor shown in FIGS. 1 and 2, taken along line 3—3 of FIG. 2.

Referring now to the drawings, and more particularly to FIG. 1, there is shown a medical instrument in the nature of an acetabular cup impactor 10 of the present invention. Impactor 10 is particular suited for use in minimally invasive surgical procedures, such as total hip arthroplasty, performed through small surgical incisions. Impactor 10 generally includes a handle 12, a surgical implement coupler 14, and an elongated shaft assembly 16 extending generally between handle 12 and surgical implement coupler 14.

Handle 12 includes a handle shaft 20 having a manual grip 22 thereon, manual grip 22 being of a size and shape for grasping in a hand to stabilize impactor 10. At an exposed end 24 of handle 12, a striker plate 26 is provided. Striker plate 26 generally covers entire exposed end 24, and is joined to handle shaft 20 such that mallet blows applied to striker plate 26 are transferred to handle shaft 20. Handle shaft 20 extends beyond manual grip 22 at an inner end 28 of handle 12 opposite striker plate 26, and is connected to elongated shaft assembly 16, as will be described in greater detail hereinafter.

Surgical implement coupler 14 is adapted for selective attachment to and detachment from an orthopedic device such as an acetabular cup (not shown). Advantageously, surgical implement coupler 14 includes a threaded stud 30 rotatably disposed in and retained by a sleeve 32. Threaded stud 30 is adapted for threaded engagement with an acetabular cup or other orthopedic device (not shown). A universal joint or swivel drive 34 is disposed rotatably in shaft assembly 16 and is drivingly connected to threaded stud 30 such that rotation of swivel drive 34 causes rotation of threaded stud 30 in sleeve 32. Various different types of swivel drives 34 are known to those skilled in the art, and will not be described in greater detail herein.

Elongated shaft assembly 16 includes a hollow outer shaft 40 having a first end 42 connected to handle 12, and a second end 44 connected to surgical implement coupler 14. Swivel drive 34 is disposed generally at second end 44, for rotation therein. First end 42 includes a yoke 46 connected between hollow shaft 40 and handle shaft 20. Yoke 46 is joined to hollow shaft 40 by way of a nipple 48 of yoke 46 engaged in hollow shaft 40, and to handle shaft 20 by means of internal threads 50 of a boss 52 on yoke 46 engaging external threads 54 on handle shaft 20.

A thumb wheel 60 or other manual activation, rotary drive input device is mounted in yoke 46 for rotation therein. A flexible drive shaft 62 is connected at one end to thumb wheel 60, and at an opposite end to swivel drive 34. One or more set screw 64 can be used to secure a first end 66 of flexible drive shaft 62 in thumb wheel 60. From thumb wheel 60, flexible drive shaft 62 extends through nipple 48 and hollow outer shaft 40, terminating at the connection to swivel drive 34. A receiver 68 from swivel drive 34 is adapted to receive a second end 70 of flexible drive shaft 62. Second end 70 is secured in receiver 68 by, for example, attachment such as crimping of receiver 68, compression from a set screw (not shown) direct adherence from adhesives, solder or welding, combinations of these techniques, or the like. Flexible drive shaft 62 thereby interconnects thumb wheel 60 with swivel drive 34 such that rotation of thumb wheel 60 causes equivalent rotation of swivel drive 34, and threaded stud 30 connected to swivel drive 34.

Striker plate 26, handle shaft 20, yoke 46 and outer shaft 40 are constructed of rigid material, such as metal, to withstand the force from blows of a mallet or the like, and to conduct the force to surgical implement coupler 14 and an acetabular cup (not shown) or other orthopedic device secured to coupler 14.

As shown most clearly in FIGS. 1 and 3, hollow outer shaft 40 has a curved portion 80 between yoke 46 and surgical implement coupler 14. Surgical implement coupler 14 and yoke 46 are in substantial linear alignment, with curved portion 80 of outer shaft 40 permitting proper alignment between handle 12 and surgical implement coupler 14 for the application of force to an acetabular cup, or the like, even as elongated shaft assembly 16 is positioned around anatomical features of a patient being operated on.

Drive shaft 62 as shown is flexible through out its length; however, it should be understood that drive shaft 62 is required to be flexible only along lengths thereof extending through curved portion 80, and as necessary to feed drive shaft 62 into outer shaft 40. Along straight lengths of outer shaft 40, drive shaft 62 can be rigid. Flexibility in drive shaft 62 is required only to allow rotation thereof within curved portion 80, although the entire length of drive shaft 62 can be flexible, if so desired. Drive shaft 62 can be conventional wound-wire flexible shafting, with alternating layers wound in opposite directions. A protective sheath (not shown) can be provided thereon. Other types of flexible shafting also can be used. Spaced standoffs (not shown) and/or lubricant can be provided within outer shaft 40, to allow proper positioning of drive shaft 62 in outer shaft 40, and to reduce resistance to rotation of drive shaft 62 within outer shaft 40.

An alignment block 82 is provided on handle shaft 20, secured against yoke 46 by a lock nut 84 threaded on handle shaft 20. Alignment block 82 includes a fixture 86 adapted for holding guide pins (not shown). The manner in which such guides pins are used, positioned parallel and perpendicular to the floor, to align and position an acetabular cup in a prepared acetabulum of a properly positioned patient, is well known to those skilled in the art, and will not be described in greater detail herein.

In the use of impactor 10, an acetabular cup (not shown) is attached to surgical implement coupler 14, such as by threaded engagement on stud 30. Threaded engagement can be made by placing a threaded hole of the cup (not shown) in general position on stud 30, and rotating the stud through rotation of thumb wheel 60 and drive shaft 62. After the cup is secured on surgical implement coupler 14, the cup (not shown) and surgical implement coupler 14 are inserted through a surgical incision made in the patient, and the acetabular cup (not shown) is brought into position for seating in a previously prepared depression in an acetabulum of the patient. The curved design of shaft assembly 16 allows impactor 10 to be positioned around intervening anatomical structures between the surgical incision and the acetabulum. Impactor 10 is positioned with the intervening anatomical structures located within the space defined by curved portion 80, as the cup (not shown) is brought into final position in the prepared acetabulum.

Curved portion 80 can be provided at different locations along the length of outer shaft 40, in different radii of curvature, and can have compound curvature, to facilitate the use of impactor 10 for different types of procedures and surgical approaches. Straight portions can be provided at each end of curved portion 80, and as shown in FIG. 3 a bushing 88 can provide a straight portion leading into surgical implement coupler 14. Surgical implement coupler 14 can have different means for attachment to an acetabular cup, or other orthopedic device, but advantageously disconnects from the device by means that are activated through rotation of drive shaft 62.

Once the acetabular cup is properly positioned, it is firmly seated in place by a blow or series of blows imparted from a mallet or the like to striker plate 26. The force of the blows is conducted through handle shaft 20, yoke 46, outer shaft 40 and surgical implement coupler 14 to the acetabular cup (not shown).

After the acetabular cub is firmly seated, impactor 10 is disconnected therefrom for removal. Thumb wheel 60 is rotated, thereby rotating flexible drive shaft 62 and stud 30, to disengage stud 30 from the cup (not shown). Impactor 10 is then removed from the incision.

The present invention provides an acetabular cup impactor that can deliver force properly to seat an acetabular cup in a prepared acetabulum, even with intervening anatomical structures disposed between the surgical incision and the acetabulum.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A surgical tool for connecting to a surgical implement, comprising:
   a hollow elongated outer shaft having a first end and a second end, said outer shaft having a curved portion between said first and second ends;
   a handle at one said end of said outer shaft;
   an implement coupler at the other said end of said outer shaft, said coupler adapted for selectively engaging and disengaging a surgical implement;
   said outer shaft, said handle and said coupler being of sufficient rigidity and strength to transmit force of impacts against said handle to an implement held by said coupler;
   a flexible drive shaft disposed in said outer shaft, one end of said drive shaft connected to said coupler for operating said coupler by rotation of said drive shaft; and
   a manual activation device including means for rotating said drive shaft to selectively operate said coupler, for selectively engaging and disengaging an implement from said coupler, said manual activation device disposed near said handle.

2. The surgical tool of claim 1, said handle having an end, and a striker plate on said handle end.

3. A surgical tool for connecting to a surgical implement, comprising:
   a hollow elongated outer shaft having a first end and a second end, said outer shaft having a curved portion between said first and second ends;
   a handle at one said end of said outer shaft;
   an implement coupler at the other said end of said outer shaft, said coupler adapted for selectively engaging and disengaging a surgical implement;
   said outer shaft, said handle and said coupler being of sufficient rigidity and strength to transmit force of impacts against said handle to an implement held by said coupler;
   a flexible drive shaft disposed in said outer shaft, one end of said drive shaft connected to said coupler for operating said coupler by rotation of said drive shaft;
   a manual activation device for rotating said drive shaft to selectively operate said coupler, said manual activation device disposed near said handle; and
   said manual activation device comprising a thumb wheel disposed near said handle.

4. The surgical tool of claim 3, said handle having an end and a striker plate on said handle end.

5. The surgical tool of claim 3, said outer shaft defining a yoke, and said thumb wheel rotatably disposed in said yoke.

6. The surgical tool of claim 3, said handle having an end, and a striker plate on said handle end.

7. The surgical tool of claim 3, said coupler including a threaded post.

8. The surgical tool of claim 7, said handle having an end, and a striker plate on said handle end.

9. A surgical tool for connecting to a surgical implement, comprising:
   a hollow elongated outer shaft having a first end and a second end, said outer shaft having a curved portion between said first and second ends;
   a handle at one said end of said outer shaft;
   an implement coupler at the other said end of said outer shaft,
   said coupler including a threaded post;
   said coupler adapted for selectively engaging and disengaging a surgical implement;
   said outer shaft, said handle and said coupler being of sufficient rigidity and strength to transmit force of impacts against said handle to an implement held by said coupler;
   a flexible drive shaft disposed in said outer shaft, one end of said drive shaft connected to said coupler for operating said coupler by rotation of said drive shaft; and
   a manual activation device for rotating said drive shaft to selectively operate said coupler, said manual activation device disposed near said handle.

10. An orthopedic impactor, comprising:
    an elongated hollow outer shaft;
    a coupler at one end of the said outer shaft adapted for engaging an orthopedic implant;
    a handle disposed at an end of said hollow outer shaft opposite from said coupler;
    a striker plate disposed on said handle, said striker plate, said handle and said outer shaft having sufficient strength and rigidity and being interrelated one with another for receiving and withstanding blows from a mallet while transmitting force from the blows to said coupler and an implant engaged thereon;
    a flexible drive shaft disposed in said outer shaft and connected to said coupler; and
    a rotary input device for rotating said drive shaft to operate said coupler to engage and disengage said coupler and the orthopedic implant.

11. A surgical impactor comprising:
an elongated hollow outer shaft;
a coupler at one end of the said outer shaft adapted for engaging an orthopedic implant;
a handle disposed at an end of said hollow outer shaft opposite from said coupler;
a striker plate disposed on said handle, said striker plate adapted for receiving blows from a mallet;
a flexible drive shaft disposed in said outer shaft and connected to said coupler;
a rotary input device for rotating said drive shaft to operate said coupler; and
a yoke disposed between said handle and said hollow outer shaft, and a thumb wheel rotatably disposed in said yoke, said thumb wheel being connected to said flexible drive shaft for rotating said drive; and
said outer shaft, said coupler, said handle and said yoke being of sufficient rigidity and strength to transmit force of impacts against said handle to an implant held by said coupler.

12. The surgical impactor of claim 11, said hollow outer shaft having straight portions at each said end and a curved portion between said straight portions.

13. The surgical impactor of claim 11, said coupler including a threaded shaft.

14. A surgical impactor comprising:
an elongated hollow outer shaft;
a coupler at one end of the said outer shaft adapted for engaging an orthopedic implant;
a handle disposed at an end of said hollow outer shaft opposite from said coupler;
a striker plate disposed on said handle, said striker plate adapted for receiving blows from a mallet;
said outer shaft, said coupler and said handle being of sufficient rigidity and strength to transmit force of impacts against said handle to an implant held by said coupler;
a flexible drive shaft disposed in said outer shaft and connected to said coupler;
a rotary input device for rotating said drive shaft to operate said coupler; and
said coupler including a threaded shaft.

15. An acetabular cup impactor, comprising:
a hollow rigid outer shaft having at least a portion defining a curved shape;
a coupler at one end of said shaft adapted for rotation to be engaged to and disengaged from an acetabular cup;
a handle at an opposite end of said shaft from said coupler, said handle having an exposed end and a striker plate on said exposed end, said striker plate, said handle and said outer shaft having sufficient strength and rigidity and being interrelated one with another for receiving and withstanding blows from a mallet while transmitting force from such blows to an acetabular cup engaged on said coupler;
a flexible drive shaft in said outer shaft connected to said coupler for rotating said coupler; and
a drive means near said handle for rotating said drive shaft to operate said coupler for engaging and disengaging an acetabular cup.

16. An acetabular cup impactor comprising:
a hollow rigid outer shaft having at least a portion defining a curved shape;
a coupler at one end of said shaft adapted for rotation to be engaged to and disengaged from an acetabular cup;
a handle at an opposite end of said shaft from said coupler, said handle having an exposed end and a striker plate on said exposed end said striker plate adapted and arranged with said outer shaft and said coupler for receiving mallet blows on said striker plate and for transmitting the force from such blows to an acetabular cup engaged on said coupler;
a flexible drive shaft in said outer shaft connected to said coupler for rotating said coupler; and
a drive means near said handle for rotating said drive shaft; and
including a yoke disposed between said handle and said hollow outer shaft, said yoke having a rigid outer frame, and a thumb wheel rotatably disposed in said yoke and connected to said flexible drive shaft for rotating said flexible drive shaft.

17. An acetabular cup impactor comprising:
a hollow rigid outer shaft having at least a portion defining a curved shape;
a coupler at one end of said shaft adapted for rotation to be engaged to and disengaged from an acetabular cup;
a handle at an opposite end of said shaft from said coupler, said handle having an exposed end and a striker plate on said exposed end said striker plate adapted and arranged with said outer shaft and said coupler for receiving mallet blows on said striker plate and for transmitting the force from such blows to an acetabular cup engaged on said coupler;
a flexible drive shaft in said outer shaft connected to said coupler for rotating said coupler; and
a drive means near said handle for rotating said drive shaft;
including a yoke disposed between said handle and said hollow outer shaft, said yoke having a rigid outer frame, and a thumb wheel rotatably disposed in said yoke and connected to said flexible drive shaft for rotating said flexible drive shaft; and
said coupler including a threaded shaft connected to said drive shaft.

18. The acetabular cup impactor of claim 17, including a universal joint between said drive shaft and said threaded shaft.

19. The acetabular cup impactor of claim 18, including a handle shaft connected to said striker plate and said yoke.

20. The acetabular cup impactor of claim 19, including a grip disposed on said handle shaft.

* * * * *

UNITED STATES PATENT AND TRADEMARK OFFICE
CERTIFICATE OF CORRECTION

PATENT NO. : 7,004,946 B2  Page 1 of 1
APPLICATION NO. : 10/283993
DATED : February 28, 2006
INVENTOR(S) : Parker et al.

It is certified that error appears in the above-identified patent and that said Letters Patent is hereby corrected as shown below:

COLUMN 6
    At line 22, please delete "3", and insert therefore --5--; and
    At line 24, please delete "3", and insert therefore --5--.

Signed and Sealed this

Twenty-eighth Day of November, 2006

JON W. DUDAS
*Director of the United States Patent and Trademark Office*